(12) United States Patent
Schoon et al.

(10) Patent No.: US 6,596,263 B1
(45) Date of Patent: Jul. 22, 2003

(54) CYCLODEXTRIN COMPOSITIONS

(75) Inventors: Douglas Schoon, Laguna Beach, CA (US); D. Russell Pflueger, Laguna Beach, CA (US)

(73) Assignee: STC English Ideas, Inc., Irvine, CA (US)

(*) Notice: Subject to any disclaimer, the term of this patent is extended or adjusted under 35 U.S.C. 154(b) by 1569 days.

(21) Appl. No.: 08/502,826

(22) Filed: Jul. 14, 1995

(51) Int. Cl.[7] .................... A61K 7/00; A61K 7/025
(52) U.S. Cl. .................. 424/64; 424/401; 514/546; 514/844
(58) Field of Search ............... 424/64, 401; 514/546, 514/844

(56) References Cited

U.S. PATENT DOCUMENTS

| | | | |
|---|---|---|---|
| 4,105,783 A | * | 8/1978 | Yu et al. .................... 424/283 |
| 4,327,147 A | | 4/1982 | Ou-Yang .................... 156/69 |
| 4,352,794 A | | 10/1982 | Koch ........................ 424/180 |
| 4,507,319 A | * | 3/1985 | Barratt et al. ............... 514/546 |
| 4,565,807 A | | 1/1986 | Uekama et al. .............. 514/58 |
| 4,616,008 A | | 10/1986 | Hirai et al. ................. 514/200 |
| 4,891,361 A | * | 1/1990 | Hatae ........................ 514/58 |
| 4,994,273 A | | 2/1991 | Zentner et al. ............. 424/422 |
| 5,324,750 A | * | 6/1994 | Lincoln et al. ............. 514/570 |

OTHER PUBLICATIONS

Angew Chemie, Int.Ed. V. 19 (1980) p. 344–362.
American Maize Products Co. (1991).
Academic Press Inc. (1984) vol. 3, p. 331–390.
Academic Press Inc. (1984) vol. 3, p. 391–440.
Academic Press Inc. (1984) vol. 2, p. 231–258.

\* cited by examiner

*Primary Examiner*—James M. Spear
*Assistant Examiner*—Rachel M. Bennett
(74) *Attorney, Agent, or Firm*—Stout, Uxa, Buyan & Mullins, LLP; Frank J. Uxa

(57) ABSTRACT

A composition comprising cyclodextrin and an α-hydroxy acid complexed by the cyclodextrin. A pharmaceutical preparation comprising a cyclodextrin-α-hydroxy acid complex and a pharmaceutically acceptable adjuvant. A combination of a cyclodextrin/α-hydroxy acid complex and an applicator having an applicator head with alternating grooves and ridges disposed on the applicator head. A method of treating a skin area comprising applying a cyclodextrin/α-hydroxy acid complex to the skin area in a pharmaceutically effective amount.

20 Claims, 1 Drawing Sheet

CYCLODEXTRIN COMPOSITIONS

BACKGROUND OF THE INVENTION

This invention relates to novel compositions for treating skin tissues, particularly human skin tissues subject to drying, chapping, abrasion, and other forms of irritation. This invention specifically relates to sustained-release compositions for treating the skin tissues described above.

α-hydroxy acids are commonly used in cosmetic formulations to treat skin tissue, frequently as an adjunct with other ingredients. The acids are used to remove dead and dying skin cells and produce a treated skin surface with a more healthy, youthful appearance. Some specific α-hydroxy acid formulations have been used in shampoos, facial creams, and cuticle creams. α-hydroxy acids, despite their beneficial properties, can nevertheless be irritating to body tissue if applied in too high a dosage or if applied to body tissue which is particularly sensitive to the acids.

Cyclodextrins are another class of compounds used in a variety of formulations to provide a sustained or controlled release of chemicals which can be complexed or chemically bound by the cyclodextrins. Cyclodextrins have been used in agricultural fertilizer and biocide formulations to control the release of biocides and fertilizers for the plants. Many chemical processes are also capable of being regulated and controlled through the use of cyclodextrin complexes which release chemical reactants in a graduated manner to control and sustain a desired property of the composition. Corrosion inhibitors and preservatives are examples of such compositions. Because of their complexing properties, cyclodextrins can be used to remove certain materials from other substances. Undesirable color and odors from processed foods, as well as undesirable ingredients such as caffeine from coffee, are examples. And because of their ability to release complexed materials gradually from the cyclodextrin molecule, cyclodextrins have been used in pharmaceutical compositions to enhance and control the bioavailability of active pharmaceutical compounds to the patient. Also, as with foods, cyclodextrins can be used to remove undesirable odors and tastes from pharmaceutical compositions.

Chemically, cyclodextrins are a group of cyclic oligosaccharides built up from a number of glucopyranose rings. The most common of the cyclodextrins are produced from six, seven, or eight glucopyranose rings and are referred to as α-, β-, and γ-cyclodextrins. Cyclodextrins have some degree of water solubility, and this is a property which ordinarily is advantageously used to produce their complexing ability with other molecules, referred to as guests. The term "guest" is used to refer to the compound which is trapped and complexed within the cyclodextrin molecule. In addition to the use of water as a solvent, other solvents can be used to permit cyclodextrins to form complexes with a number of other guests which may not be complexed using water with cyclodextrins.

Cyclodextrins perform their many complexing functions because of their molecular structure. Their molecular structure can be analogized to that of a doughnut—a cylindrical configuration with a cavity or hole in its center. The materials to be complexed are trapped within the hole or cavity of the cyclodextrin molecules and held there through a number of different binding mechanisms. The size of the hole or cavity, both its diameter and depth, is influenced by the number of glucopyranose rings in the cyclodextrin molecule, and the size of the cavity plays a critical role in the complexing of different chemical compounds. Although it is commonplace to have an approximately equimolar ratio of guest molecules to cyclodextrin molecules, it is equally possible to have, in the case of some low molecular weight molecules, more than one guest molecule complexed within the cyclodextrin molecular cavity. On the other hand, if the cavity is too large and the guest is too small, the guest may pass through the cavity and not be bound at all. With some high molecular weight guests, more than one cyclodextrin molecule can be required to form an adequate and complete complex with the guest. But if the guest molecule is too large for the cyclodextrin cavity, even several cyclodextrin molecules may not be able to bind the guest to temporarily inactivate its active moieties. This, in turn, produces an ineffective complexing of the guest and an ineffective controlled release of the formulation. This may be satisfactory if the partially complexed guest is to be removed because of its undesirability in the final formulation, but is quite unsatisfactory if the guest is complexed with the expectation that its activity will slowly be released upon use.

As a consequence of the cyclodextrin molecular cavity, the guest to be complexed, the reason for the complexing and the solubility of the guest in water or other solvents, it is not always possible to predict which guest molecules can be complexed by which cyclodextrin molecules to produce a particular desired effect. Considering the intended use of the cyclodextrin-guest composition and the environmental conditions under which the composition will be used, it becomes even more difficult to predict whether any chosen cyclodextrin formulation will perform adequately for its intended purpose.

SUMMARY OF THE INVENTION

The present invention relates to a cyclodextrin composition comprising a cyclodextrin and an α-hydroxy acid wherein the α-hydroxy acid is complexed by the cyclodextrin. The invention further relates to the use of the above composition to treat skin tissue, particularly skin tissue on, beneath and around the eyes, and the lips. The invention further relates to the above composition in combination with a ribbed applicator of the type shown in the accompanying drawings. The invention also relates to a topical pharmaceutical or cosmetic composition comprising the above composition and a pharmaceutically or cosmetically acceptable adjuvant for treating or applying to skin tissue. Finally, this invention relates to a method for treating skin tissue comprising the application of the above topical composition to skin tissue.

Without wishing to limit the invention to any particular theory of operation, it is believed that the α-hydroxy acid or acids in the present compositions are gradually, over time on the skin, released from the cyclodextrin to benefit the skin. This "sustained release" feature allows the composition to be applied only once or twice daily (it can be applied more frequently if desired) and still get substantially continuous benefits. The present combination of α-hydroxy acid/cyclodextrin can advantageously be included in cosmetic products, for example, lip make-up or eye make-up, so that such products provide an immediate cosmetic appearance enhancement while, at the same time, providing longer term benefits to the skin. The α-hydroxy acids are believed to penetrate the skin, if at all, to only a very limited extent.

BRIEF DESCRIPTION OF THE DRAWINGS

The present invention can be more readily understood from the accompanying drawings in which.

DETAILED DESCRIPTION OF THE INVENTION

Figure 1:
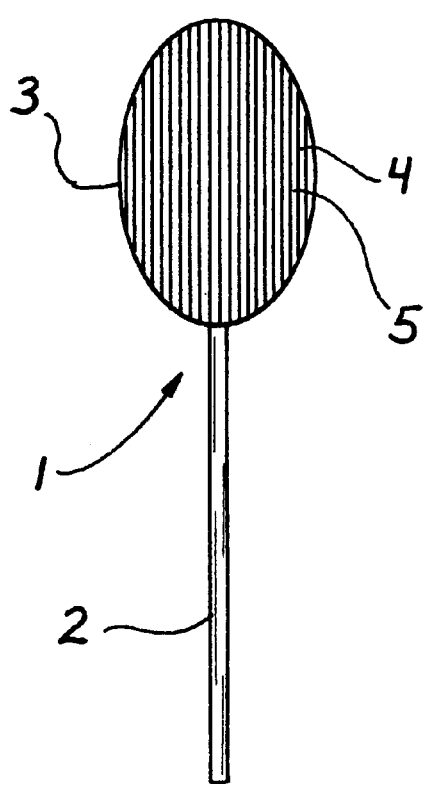
FIG. 1 is a top plan view of the applicator which can be used to apply the cyclodextrin composition of this invention.

Compositions of the present invention comprise a cyclodextrin, meaning to include one or more cyclodextrins, one or more cyclodextrin derivatives or substitute cyclodextrins and mixtures thereof, and an α-hydroxy acid, meaning to include one or more α-hydroxy acids, one or more α-hydroxy acid derivatives or substituted α-hydroxy acids and mixtures thereof, complexed by the cyclodextrin.

Cyclodextrins are a group of cyclic non-reducing oligosaccharides built up from a number of glucopyranose rings. As many as 14 or 16 glucopyranose rings can be used. In commercial applications, the number of rings available in commercially available cyclodextrins is usually six, seven, or eight, and are referred to as α-, β-, and γ-cyclodextrins. Cyclodextrins have a doughnut-shaped molecular configuration, with the cyclic oligosaccharides arranged in a circular configuration around a hole or cavity. The size of the hole or cavity has an effect upon the type of guest molecules which can be effectively complexed by the cyclodextrin. α-cyclodextrin has a cavity diameter of about 5 Å; β-cyclodextrin has a cavity diameter of about 6.25 Å; and γ-cyclodextrin has a cavity diameter of about 8 Å. The depth of the cavity will vary only slightly among the three forms, and will be about 7.5 to 8.5 Å.

In general, the cyclodextrin is present in an amount effective to complex at least a portion, preferably at least a major portion, of the α-hydroxy acid present. The cyclodextrin preferably comprises from about 10 to about 95 or more % by weight of the total α-hydroxy acid and cyclodextrin present. More preferably, the cyclodextrin comprises from about 15 to about 80%, and even more preferably from about 20 to about 75%, by weight of the total α-hydroxy acid and cyclodextrin present.

Cyclodextrins have some solubility in water and/or a number of solvents. The type of non-aqueous solvents useful herein depends somewhat upon the particular cyclodextrin chosen. In general, glycerin, ethylene glycol, propylene glycol, ethyl alcohol, methanol, dimethyl sulfoxide, dimethyl formamide, and N-methyl pyrrolidone have been found to solubilize the cyclodextrin and many of the α-hydroxy acids used herein.

The amount of solvent used to dissolve the cyclodextrin and the α-hydroxy acid is variable over a wide range. The solvent, if it is water, can be from about 10% or less up to as much as about 75% by weight of the total α-hydroxy acid, cyclodextrin and solvent present. For preferred formulations, the amount of water ranges from about 20% to about 60% by weight of the total α-hydroxy acid, cyclodextrin and solvent present. If the solvent is a non-aqueous solvent, the percentage amount depends, for example, upon the solubility of the cyclodextrin and the α-hydroxy acid in the solvent. For most compositions, the amount of a non-aqueous solvent is within the same percentages as that specified for water.

The α-hydroxy acids useful herein include, but are not limited to, monobasic and multibasic acids, preferably having from about 2 to about 20 or more carbon atoms per molecule. Examples include glycolic acid, malic acid, citric acid, lactic acid, α-hydroxy stearic acid, α-hydroxy oleic acid, and α-hydroxy linoleic acid and the like and mixtures thereof. More preferred are glycolic, malic, citric, and lactic acids and mixtures thereof.

In general, the α-hydroxy acid is present in the present compositions in an amount effective to provide at least one beneficial effect to the skin area to which the composition is applied. The α-hydroxy acid preferably comprises from about 1 to about 40 or even 50% by weight of the total α-hydroxy acid and cyclodextrin present, and a preferred range is from about 2 to about 40% by weight of the total α-hydroxy acid and cyclodextrin present. It is often convenient to define the useful limits of the α-hydroxy acids in terms of their percentages of the cyclodextrins present. The α-hydroxy acid is preferably present in an amount of from about 10 to about 120% by weight, of the cyclodextrin present, and more preferably from about 25 to about 75% by weight, or about 35 to about 150 mole %, of the cyclodextrin present.

At least a portion of the α-hydroxy acid is complexed by the cyclodextrin. This means that the α-hydroxy acid is bound to, or otherwise interacts with, the cyclodextrin in such a manner that the activity of the α-hydroxy acid is suppressed or totally negated for some period of time or for so long as the complex remains intact. The nature of the complex is dynamic with the equilibrium being such that the α-hydroxy acid is often gradually released from, the cyclodextrin and therefore gradually becomes available to exhibit its beneficial properties.

In one embodiment, the compositions of the present invention comprise three principal ingredients, cyclodextrin, α-hydroxy acid, and solvent. Preferably, such compositions include from about 10 to about 70% cyclodextrin, from about 3 to about 35% α-hydroxy acid, and from about 10 to about 80% solvent, all by weight percent of the total cyclodextrin, α-hydroxy acid and solvent present.

The present invention also relates to the use of a topically applied pharmaceutical or cosmetic preparation comprising the cyclodextrin-α-hydroxy acid formulations described above in combination with a pharmaceutically or cosmetically acceptable adjuvant to facilitate the application of the preparation and/or enhance its performance. Suitable adjuvants include petrolatum, waxes and oils, menthol, camphor, alum, salicylic acid, phenol, fragrances, coloring agents, lanolin, cocoa butter, water-soluble polymers as thickeners, and the like. Hence, adjuvants can be inert carriers for the active composition, as well as active themselves in promoting the desired effect upon the skin area to which the preparation or formulation is applied. The amount of adjuvant used depends upon the intended use of the formulation. To permit easy application of the composition to skin tissue and prevent it from leaving the skin in a liquid condition, it is advisable that the topical pharmaceutical preparation have a viscosity or thickness sufficient to permit the preparation to remain on the site to which it is applied. The preparation may have a consistency permitting it to remain in a preformed shape, at least until pressure is applied to transfer the preparation to the skin tissue to which the preparation or formulation is applied. Petrolatum, and waxes modified with oils, are preferred for placing the preparation in a solid shape suitable for applying it to a skin surface. If the preparation is to be formulated in a viscous form similar to facial creams, there are a number of cosmetic oils which can be used in combination with, or in substitution for, the waxes and the water-soluble polymers.

The pharmaceutical or cosmetic preparations of the present invention are particularly suited for application to skin surfaces sensitive to treatments. Lips, eyelids, areas around and beneath the eyes, rectum, and squamous tissue are examples of tissues which can be advantageously treated. The α-hydroxy acids in too high a concentration can be especially aggressive and irritating to sensitive skin. The complexing of the acids with cyclodextrin is particularly beneficial since it inhibits the application of too high a concentration of the acids, while at the same time making it possible to apply, over a sustained period of time, a pharmaceutically effective amount of the α-hydroxy acid to the site to be treated. In certain instances, it is preferred to include α-hydroxy acid which is not complexed or which is free of the cyclodextrin. Such compositions are particularly useful when it is desired to provide a substantial immediate benefit (from the α-hydroxy acid) to the area to which the preparation or formulation is applied. The use of free α-hydroxy acid allows this immediate benefit over a prolonged period of time because of the sustained release feature of the present invention.

The amount of pharmaceutically or cosmetically acceptable adjuvant can, as stated above, vary widely in the preparations. If the preparation is to be prepared in a solid form, such as a stick for application to lips, the preparation may contain as much as about 75% or more wax and petrolatum adjuvant. If the preparation or formulation is prepared in a cream or gel condition, it is possible that the amount of adjuvant may be as little as about 5% or less by weight of the total preparation. In the present preparations, it is important that the active ingredient or ingredients be present in an amount sufficient to provide the desired effect or effects. Depending upon the α-hydroxy acid and the cyclodextrin used, the α-hydroxy acid is usually present in an amount from about 0.1 to about 20%, preferably about 0.3 to about 15%, by weight of the total preparation or formulation. The term "pharmaceutical preparation" includes compositions where the therapeutic benefits are so moderate or so transient that the benefits may be considered as cosmetic instead of therapeutic in the clinical sense. In fact, one of the principal benefits of the preparations of this invention arises because of its activity on skin where the major activity is limited to the outermost layer of the skin and is temporary and short-acting.

Figure 2:
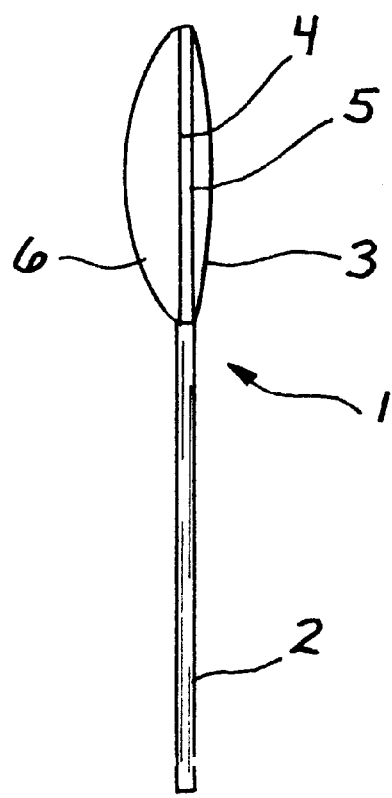
FIG. 2 is a side view of the applicator.

The pharmaceutical preparations can be applied to the area to be treated with an applicator of the type shown in the accompanying drawings. FIG. 1 is a plan view of an applicator, shown generally at 1, viewed from the top of the applicator. Applicator 1 has a handle 2 and an applicator head 3. Head 3 contains a plurality of ridges 4 and grooves 5. FIG. 2 shows both sides of the applicator head 3 are shown. Side 6 opposing the side with the ridges 4 and grooves 5 can be smooth to provide an alternate surface for application of the preparation to a skin area to be treated. The smooth side and the ridged side, and the angle of the ridges to the skin surface as the applicator is moved along the skin surface, afford a number of ways in which the formulation can be applied to the skin surface in different amounts and thicknesses. Hence the present invention also includes, in combination, with an applicator having an applicator head, with a plurality of grooves and ridges on at least a portion of the surface of the head, and a pharmaceutical preparation in accordance with the present invention on the applicator head.

The present invention also includes a method for treating skin tissue comprising applying a pharmaceutically effective amount of a composition comprising cyclodextrin and an α-hydroxy acid wherein the α-hydroxy acid is complexed by the cyclodextrin. Preferred compositions contain one or more of the pharmaceutical or cosmetic adjuvants described above.

Compositions of this invention can be prepared by first combining the cyclodextrin and α-hydroxy acid in a suitable solvent such as water, glycerin and the like. The term "dissolving" should be broadly construed to include the formation of a paste or a slurry in which the cyclodextrin and α-hydroxy acid are mixed with a solvent to provide a substance which is less than a complete solution. It is preferred that the cyclodextrin and α-hydroxy acid are completely soluble in the solvent, particularly at about room temperature. Also included is a method in which the cyclodextrin and α-hydroxy acid are mixed with little or no added water other than the water of hydration present in the ingredients, or water simply absorbed by the ingredients. The α-hydroxy acid, cyclodextrin and water are mixed, placed in a sealed or covered container, and optionally heated with additional mixing, preferably at a temperature from about 10° C. to about 45 or about 50° C., preferably from about ambient to about 30 to 40° C., for a period of time to achieve effective α-hydroxy acid/cyclodextrin complexing. The time will vary depending upon the choice of ingredients, and their relative proportions. Some of the preferred compositions of this invention have been prepared at room temperature, for example, about 20 to 25° C., with the length of time in the range of about 12 to about 24 hours. For a glycolic acid, α-cyclodextrin, and water mixture where the three ingredients are present in approximately equal proportions, it is acceptable to use a temperature of about 60 to 110° C. for about one to about eight hours. Other mixtures, using a combination of naturally derived α-hydroxy acids and hydroxy β-cyclodextrin complexed in water or glycerin, have been complexed at temperatures from about 10° C. to about 45° C. for times from about 3 hours or about 12 hours to about 24 hours or more.

It has been found that many, if not all, of the useful α-hydroxy acids are sensitive to elevated temperatures, that is decompose or otherwise degrade if exposed to elevated temperatures for prolonged periods of time. However, elevated temperatures promote the complexing of α-hydroxy acids and cyclodextrins. In order to maintain the α-hydroxy acids intact and to obtain a sufficient or acceptable amount of α-hydroxy acid/cyclodextrin complexing, it is preferred that the preparation processing be conducted at a temperature below about 50° C., more preferably from about 10° C. to about 40° C., and that the period of time be from about 12 hours or about 16 hours to about 24 hours or more.

The foregoing mixing can be carried out simply by physically blending, with mixing, the ingredients together. For example, the mixing can be carried out in an extruder where the mixing is carried out in the extruder barrel where the conditions of mixing and heating, if any, can be satisfactorily controlled. The advantage of extrusion mixing is that it can be conducted in a continuous operation and uses relatively little solvent, thereby reducing the volume of material which must be handled.

One preferred method of complexation comprises dissolving cyclodextrin completely in water or other appropriate solvent with heating, adding the α-hydroxy acid to the solution, continuing or increasing the heating of the solution, and then if necessary, cooling the solution to precipitate the cyclodextrin-α-hydroxy acid complex. The precipitate can be further purified by decantation, filtration, or washing with water or other solvent. Following separation of the precipitation cake complex from its solvent and impurities, the material can be modified with the pharmaceutical adjuvants mentioned earlier. A disadvantage is the large volume of reactants which must be mixed and handled before the water or solvent is removed from the precipitate.

Upon formation of the complexed precipitate and its drying, the complex is stable and has a long shelf or storage life as long as the complex is stored under dry conditions at or about ambient or room temperature. Ambient moisture will cause release of the α-hydroxy acid from the cyclodextrin. This property is used advantageously in the topical application of the composition to a skin site to be treated insofar as the moisture in and on the skin will cause a gradual release of the α-hydroxy acid from the cyclodextrin, thereby making it available for treatment of the area to which it has been applied.

The following non-limiting examples illustrate certain aspects of the present invention.

EXAMPLE 1

A quantity of 20 kg of cyclodextrin is mixed with 80 L of water and the mixture heated to 100° C. A quantity of 20 kg of glycolic acid is added to the solution and the mixing is continued for one hour, after which time the heat is removed and the solution is allowed to precipitate. The precipitate is washed with water and filtered. The washed precipitate is further washed with ethyl alcohol, and the alcohol decanted. The precipitate cake is then freeze-dried to remove excess water and stored in a sealed container.

EXAMPLE 2

A quantity of 10 kg of the cyclodextrin-glycolic acid complex of Example 1 is placed in a covered container and mixed with 25 kg of a wax-petrolatum base which contains 5% lanolin and 3% cocoa butter by weight of the base, 1 kg of menthol, 0.5 kg of camphor, 0.5 kg of alum, and 0.25 kg of salicylic acid. The ingredients are mixed in the covered container to exclude atmospheric moisture for a period of 30 minutes. The resultant preparation has a consistency intermediate between petroleum jelly and chilled butter, and has a glycolic acid content of 5% by weight of the total preparation. The glycolic acid is fully complexed by the α-cyclodextrin.

EXAMPLE 3

The pharmaceutical preparation of Example 2 is applied to the lips of a subject and found to provide a soothing effect with no adverse consequences.

EXAMPLE 4

A quantity of two parts by weight of an α-hydroxy acid extract in glycerin (25% by weight of a mixture of α-hydroxy acids—glycolic acid, citric acid and lactic acid—and 75% glycerin) and one part by weight of hydroxy-β-cyclodextrin is mixed with a quantity of the preservative, methyl paraben to bring the methyl paraben content to 0.5% of the total mixture. The mixture is prepared at 20° C. and let stand 24 hours at that temperature. The mixture is converted into a clear syrupy solution with an α-hydroxy acid taste greatly reduced from the taste exhibited by the acid extract in glycerin. The reduced acid taste occurs because of the complexing of the acids with the cyclodextrin.

The above solution is compounded, using one or more conventional pharmaceutically acceptable carriers, waxes, fragrances, and other additives to produce different formulations of varying consistency, for example, from a cream to a solid at room temperature. The amount of the solution used in each of these formulations ranges from 3% to 15% by weight. The processing temperature in making these formulations is maintained below 35° C. The pH of each of these formulations remains substantially constant, even after several months. This indicates that the α-hydroxy acids are not being degraded.

Each of these formulations is used by applying it to the lips and/or to the area around and beneath the eyes of a human on a daily basis over a two week period. The cream formulations are applied using the applicator illustrated in FIGS. 1 and 2. In each case, the lips and the area around and beneath the eyes have a more youthful appearance after the two-week treatment period.

EXAMPLE 5

Example 4 is repeated except that the mixture is prepared at 100° C. and allowed to stand at this temperature overnight. It is found that the α-hydroxy acids are significantly degraded by this processing, so that the final formulations are not as effective as the corresponding formulations in Example 4.

EXAMPLE 6

Example 4 is repeated except that the mixture is allowed to stand for only 4 hours. It is found that the solution has a strong α-hydroxy acid taste indicating that the complexing of the acids is not complete. The final formulations, which include α-hydroxy acids that are not complexed with the cyclodextrin, are more aggressive on the skin than the corresponding formulations in Example 4. In addition, the pH of each of the formulations increases over time, for example, about 0.5 pH units per week. This indicates that the α-hydroxy acids are being degraded.

EXAMPLE 7

Example 4 is repeated except that the amount of α-hydroxy acid extract used is in excess of that which can be complexed by the cyclodextrin used. The final formulations, which include α-hydroxy acids which are not complexed with cyclodextrin, are effective, but are somewhat more aggressive on the skin than the corresponding formulations in Example 4.

One approach to using the of formulations of Example 7 is to use such formulations on a daily basis for the first week and to then switch to the corresponding formulation of Example 4. In this manner, a more intense or aggressive treatment of the skin is initially provided, followed by a more mild treatment or care regime, which can be continued on a long term basis.

EXAMPLE 8

Example 4 is repeated except that the amount of the cyclodextrin used is substantially in excess of that needed to complex with the α-hydroxy acids. A further reduction in product acid taste is achieved, relative to the product of Example 4. The final formulation is somewhat less aggressive than the formulation of Example 4, and provides substantially similar results, after two weeks, as does the formulation of Example 4.

While this invention has been described with respect to various specific examples and embodiments, it is to be understood that the invention is not limited thereto and that it can be variously practiced within the scope of the following claims.

What is claimed is:

1. A cosmetic composition comprising a cyclodextrin and an α-hydroxy acid complexed by the cyclodextrin and present in an amount effective to remove dead and dying skin cells from skin tissue, the cyclodextrin being present in an amount effective to provide for the sustained release of the α-hydroxy acid from the cyclodextrin to remove dead and dying skin cells from skin tissue over time after the cosmetic composition is applied to skin tissue, the cosmetic composition contains about 1% to about 50% complexed α-hydroxy acid by weight based on the total cyclodextrin and α-hydroxy acid present.

2. A composition according to claim 1 wherein the composition contains from about 1% to about 40% complexed α-hydroxy acid by weight of the total cyclodextrin and α-hydroxy acid present.

3. A composition according to claim 1 wherein the composition contains α-hydroxy acid which is not complexed by cyclodextrin.

4. A composition according to claim 1 wherein the α-hydroxy acid is selected from the group consisting of glycolic acid, citric acid, males acid, lactic acid and mixtures thereof.

5. A composition according to claim 1 wherein the cyclodextrin is selected from the group consisting of, α-cyclodextrin, β-cyclodextrin, hydroxy-β-cyclodextrin, γ-cyclodextrin and mixtures thereof.

6. A composition according to claim 5 wherein the complexed α-hydroxy acid is present in an amount from about 2 to about 25% by weight of the total cyclodextrin and α-hydroxy acid present.

7. A composition comprising a cyclodextrin and an α-hydroxy acid which is complexed with the cyclodextrin, the cyclodextrin is hydroxy-β-cyclodextrin and is present in an amount of from about 15 to about 80% by weight of the total cyclodextrin and α-hydroxy acid present.

8. A cosmetic composition comprising a cyclodextrin, an α-hydroxy acid which is complexed with the cyclodextrin and is present in an amount effective to remove dead and dying skin cells from skin tissue, and a minor amount of up to 25% by weight of glycerin, the cyclodextrin being present in an amount effective to provide for sustained release of the α-hydroxy acid from the cyclodextrin to remove dead and dying skin cells from skin tissue over time after the composition is applied to skin tissue.

9. A composition according to claim 7 wherein the hydroxy-β-cyclodextrin is present in an amount of from about 20 to about 75% by weight of the total cyclodextrin and α-hydroxy acid present.

10. A composition according to claim 8 wherein the glycerin is present in the composition in an amount of from about 5 to 25% by weight of the total composition.

11. A composition according to claim 7 wherein the α-hydroxy acid is selected from the group consisting of glycolic acid, lactic acid, citric acid, malic acid and mixtures thereof.

12. A composition according to claim 1 which further comprises a pharmaceutically acceptable adjuvant.

13. A composition according to claim 12 wherein said cyclodextrin is selected from the group consisting of α-cyclodextrin, β-cyclodextrin, hydroxy-β-cyclodextrin, γ-cyclodextrin and mixtures thereof, and the α-hydroxy acid is selected from the group consisting of glycolic acid, lactic acid, citric acid, malic acid and mixtures thereof.

14. A composition according to claim 13 wherein said cyclodextrin is present in an amount of from about 0.5 to about 80% by weight of the total composition, said α-hydroxy acid is present in an amount of from about 0.1 to about 20% by weight of the total composition, and said pharmaceutical adjuvant is present in an amount of from about 5 to about 75% by weight of the total composition.

15. A combination comprising a composition according to claim 1 and an applicator, said applicator comprising a handle having two ends and an applicator head attached to one of said ends, said applicator head having a plurality of grooves and ridges disposed on said head.

16. A method for treating or caring for a skin area comprising applying to said skin area a composition according to claim 1.

17. A method according to claim 16 wherein the cyclodextrin is selected from the group consisting of α-cyclodextrin, β-cyclodextrin, hydroxy-β-cyclodextrin, γ-cyclodextrin and mixtures thereof, and the α-hydroxy acid is selected from the group consisting of glycolic acid, lactic acid, citric acid, malic acid and mixtures thereof.

18. A method according to claim 16 wherein a pharmaceutical adjuvant is present in the composition, and said skin area is at least one of the area of the lips and the area below the eye.

19. A method according to claim 16 wherein said skin area is the area of the lips and said applying includes placing a quantity of said composition on the applicator head of an applicator comprising a handle having two ends with the applicator head attached to one of said ends and having a plurality of grooves and ridges disposed thereon, and contacting the area of the lips with said applicator head and said composition.

20. Cosmetic composition containing glycolic acid in form of a controlled release inclusion complex with beta-cyclodextrin.

* * * * *